United States Patent
Lofgren

(10) Patent No.: US 6,872,219 B2
(45) Date of Patent: Mar. 29, 2005

(54) RECONSTRUCTIVE VASCULAR TREATMENT APPARATUS AND METHOD

(75) Inventor: Gunnar Torbjorn Lofgren, Fort Lauderdale, FL (US)

(73) Assignee: Aquapulse International, L.L.C., Plantation, FL (US)

( * ) Notice: Subject to any disclaimer, the term of this patent is extended or adjusted under 35 U.S.C. 154(b) by 56 days.

(21) Appl. No.: 10/464,329

(22) Filed: Jun. 18, 2003

(65) Prior Publication Data

US 2004/0015217 A1 Jan. 22, 2004

Related U.S. Application Data

(60) Provisional application No. 60/391,066, filed on Jun. 19, 2002.

(51) Int. Cl.[7] .............................. A61H 21/00; A61F 7/00
(52) U.S. Cl. .......................... 607/82; 607/85; 607/104; 607/108; 601/156; 601/160
(58) Field of Search ............................ 607/81–87, 104, 607/108, 96, 111, 156–160, 112, 114; 601/156–160; 606/112, 114

(56) References Cited

U.S. PATENT DOCUMENTS

| | | | | | |
|---|---|---|---|---|---|
| 2,826,763 | A | * | 3/1958 | Bass | 4/606 |
| 3,487,996 | A | | 1/1970 | Lofgren | |
| 4,090,507 | A | * | 5/1978 | Van Horn | 601/166 |
| 4,099,522 | A | * | 7/1978 | Alenares | 601/156 |
| 4,192,297 | A | * | 3/1980 | Labrecque | 601/166 |
| 4,620,529 | A | * | 11/1986 | Kurosawa | 601/157 |
| D289,438 | S | | 4/1987 | Lofgren | |
| 5,044,357 | A | * | 9/1991 | Johns | 601/166 |
| 5,158,076 | A | * | 10/1992 | Thomsen | 601/156 |
| 5,241,953 | A | * | 9/1993 | Sykes | 601/166 |
| 5,441,529 | A | * | 8/1995 | Dorsch | 607/82 |
| 6,428,466 | B1 | * | 8/2002 | Licht et al. | 600/27 |
| 6,623,511 | B1 | * | 9/2003 | Daffer et al. | 607/82 |

* cited by examiner

*Primary Examiner*—Roy D. Gibson
(74) *Attorney, Agent, or Firm*—Malin, Haley & DiMaggio, P.A.

(57) ABSTRACT

A vascular treatment apparatus, comprising a chair, a horizontal housing and a retractable cover. The cover has hot and cold fluid dispensers whereby alternating and pulsating sprays of hot fluid and cold fluid treat a patient. The housing section also includes hot and cold fluid dispensers. The temperature, pulse strength and pulse rate are controlled by a central processing unit. The central process unit also correlates patient information for observing patient progress and comparing with other patients. Skin conditioner and disinfectant dispensers are included. The chair swivels for easy patient entry. The inventive method includes alternating pulsing streams of hot and cold fluid, preferably alternating 3 seconds of hot fluid with 3 seconds of cold fluid. The hot fluid is between 32 degrees centigrade and 41 degrees centigrade, and the treatment duration is approximately 25 minutes. Preferably, before treatment, the temperature of the hot fluid is gradually raised.

42 Claims, 6 Drawing Sheets

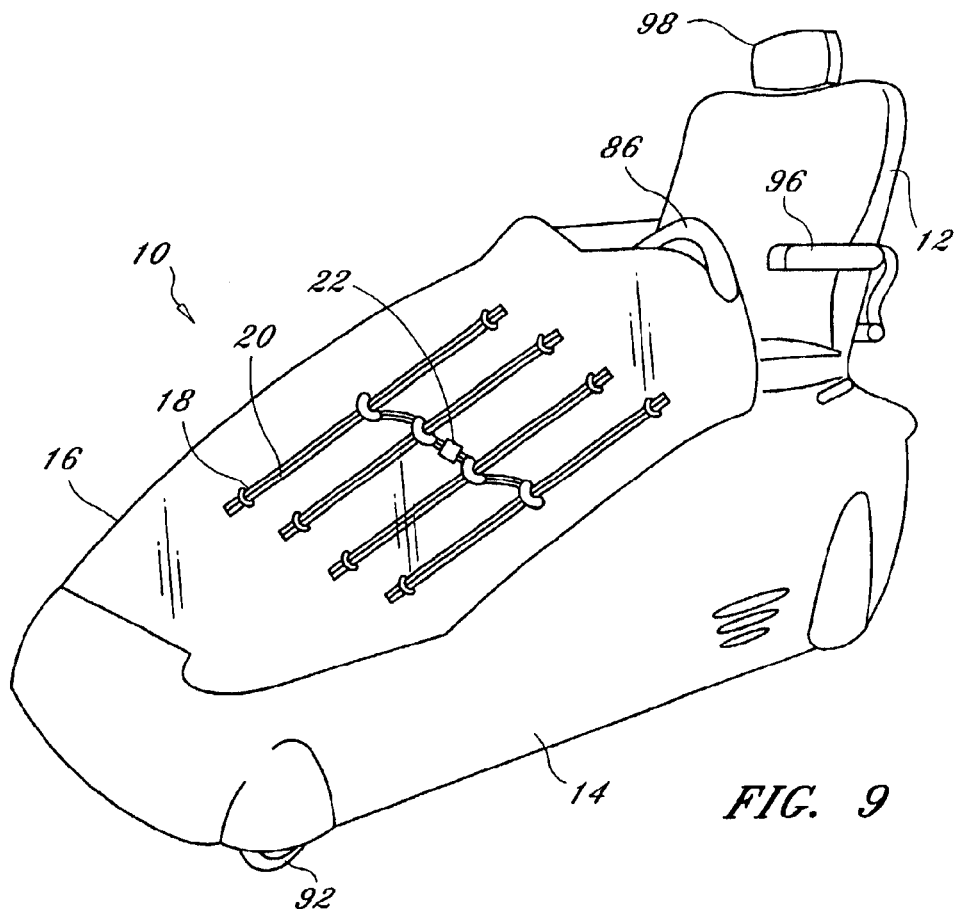
FIG. 9
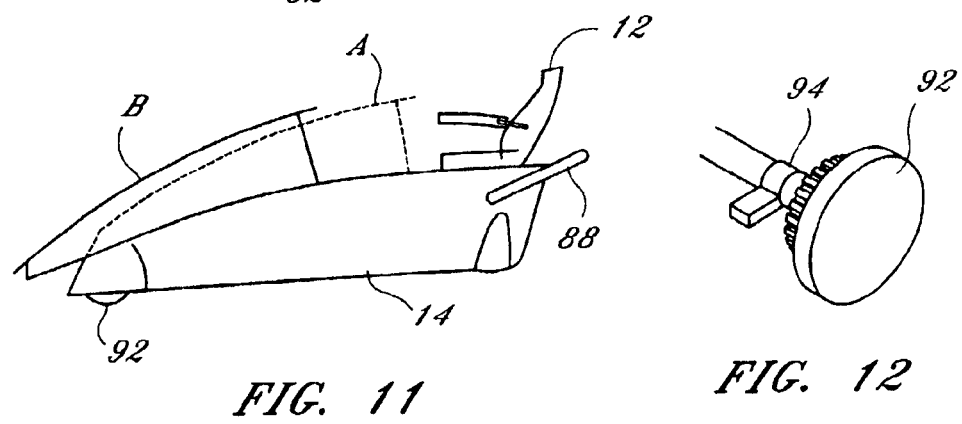
FIG. 11
FIG. 12

RECONSTRUCTIVE VASCULAR TREATMENT APPARATUS AND METHOD

This application claims priority to Provisional U.S. Patent Application Ser. No. 60/391,066, filed on Jun. 19, 2002.

BACKGROUND OF THE INVENTION

1. Field of the Invention

This invention relates generally to a reconstructive vascular treatment apparatus, and a method for vascular treatment in general. More particularly, this invention relates to an apparatus and method for treating a patient to alternating, pulsating streams of hot and cold fluid.

2. Description of Related Art

Reconstructive Vascular Treatment (RVT) is a method and system utilizing a digitized and computerized electronic operational system for the application of hot and cold fluid using exact and distinctive temperature differences applied to specific areas of the body. When the skin is exposed to alternately hot and cold temperatures, the body reacts by increasing the blood flow to the part of the body being treated. Alternation of constriction and dilatation of the local blood vessels stimulates peripheral blood-flow and helps to stimulate healing. If the treatment is systematically repeated over a period of time, the patient's blood circulation will permanently increase, due to the development of new collateral blood vessels in the body. Each blood vessel naturally has the capability for this new growth, and this growth is stimulated by the RVT.

RVT is primarily used as a type of "vascular stimulation," causing alternate vasoconstriction and vasodilatation of local blood vessels to increase peripheral blood flow, mitigate pain, and stimulate healing by utilizing the body's natural innate ability to maintain homeostasis.

Medical Terminology

Homeostasis: a tendency to stability in the normal body states (internal environment) of the organism. It is achieved by a system of control mechanisms activated by negative feedback.

Vasoconstriction: the diminution of the caliber of vessels, especially constriction of arterioles leading to decreased blood flow to a part.

Vasodilatation: a state of increased caliber of the blood vessels.

Collateral Blood Vessels: secondary or accessory; not direct or immediate, a small side branch of blood vessels.

In addition to reconstructive treatment, the inventive treatment is also beneficial to those subject to high gravitational forces, such as fighter pilots and astronauts.

SUMMARY OF THE INVENTION

It is an object of the present invention to provide an apparatus that makes available comfortable vascular treatment for a patient.

It is another object of the invention to provide an apparatus that is easy to use and easy to customize for treatment of a patient.

It is yet another object of the invention to provide an apparatus that is sturdy and provides reliable service in treatment of a patient.

It is still another object of the invention to provide an apparatus that makes improved hot and cold fluid vascular treatment of a patient.

It is yet still another object of the invention to provide an apparatus for vascular treatment of a patient that has pulsing sprays for the front and back of a person's legs.

It is yet another object of this invention to provide an apparatus that provide skin conditioner to a patient and is self cleaning after a patient is treated.

It is another object of the invention to provide an apparatus that obtains and records vascular treatment data for comparison with other patients and the observation of a patient's progress.

It is still another object of the invention to provide an apparatus for vascular treatment which is remote controlled.

It is still another object of the invention to provide an improved method for vascular treatment.

In accordance with these and other objects, the present invention comprises a vascular treatment apparatus having a chair or equivalent means for supporting a patient, a horizontal housing means for supporting plumbing and the chair means, and a retractable cover. The retractable cover includes one or more hot fluid dispensers, and one or more cold fluid dispensers, whereby pulsating sprays of hot fluid and cold fluid treat a patient. The instant invention further includes in the housing one or more housing hot fluid dispensers and one or more housing cold fluid dispensers. The housing may includes a hot fluid manifold and a cold fluid manifold for even distribution of the fluids through the dispensers.

The housing may have contoured footrests that each have individual fluid distributors, and the chair may be in swiveling connection with the housing.

The apparatus may have an adjustor for the strength and frequency of the pulsing sprays, and a temperature controller for at least one fluid. The adjustor may include a central processing unit (CPU) or other computerized means for manipulating the strength and frequency of the pulsing sprays and the temperature controller.

The apparatus may further include a disinfectant dispenser, and the hot and cold fluid dispensers in the cover, in the housing, or both, are tubular. An external motor may mix the hot fluid thereby adjusting the hot fluid temperature.

The apparatus may further include an intake for hot fluid, an intake for cold fluid, and a mixing chamber located downstream from the intake for hot media capable of receiving cold fluid from the intake of cold fluid. The hot fluid dispensers and the cold fluid dispensers each may include at least one magnetic valve for controlling flow.

The retractable cover may slide across the horizontal housing section or open by a hinging means. Also, the apparatus may have a handlebar for the patient, for the operator, or both. In addition, the apparatus may include a dispenser of skin conditioner.

The preferred method for providing vascular treatment of the invention includes the steps of placing a patient in a vascular treatment apparatus, including chair means for supporting a vascular treatment patient, horizontal means for housing plumbing located below the chair means and a retractable means for covering a patient including a first means for treating a patient on the chair with alternating pulsing streams of hot fluid and cold fluid located above the body means. The next step is of treating the patient with alternating pulsing streams of hot fluid and cold fluid.

The means for housing may further include a second means for treating a patient on the chair with alternating pulsing streams of hot fluid and cold fluid. This second means may include a hot fluid manifold and a cold fluid manifold.

Preferably, the step of treating comprises alternating approximately 3 seconds of hot fluid with approximately 3 seconds of cold fluid. It is preferred that the fluid is water. The hot fluid is preferred to be approximately between 32 degrees centigrade and 41 degrees centigrade, and the duration of the step for treating is approximately 25 minutes. Before treatment, the temperature of the hot fluid is preferably gradually raised over a pre-determined period of time before the step of treating, to make the patient comfortable with the raised temperature of the hot fluid.

The pulsing streams of hot fluid and cold fluid is preferably controlled by a computer, and the computer is preferably in electronic communication with magnetic valves for controlling the flow of hot fluid and the flow of cold fluid. Alternatively, the treatment may be optimized for the depilatory effect on the patient.

In accordance with these and other objects which will become apparent hereinafter, the instant invention will now be described with particular reference to the accompanying drawings.

BRIEF DESCRIPTION OF THE DRAWINGS

FIG. 9 shows a perspective view of an alternative embodiment of the invention with the cover closed.

FIG. 11 shows a side view of an alternative embodiment of the invention illustrating the movement of the cover.

FIG. 12 is a detail view of a wheel assembly of an alternative embodiment of the invention.

DETAILED DESCRIPTION

Figure 1:
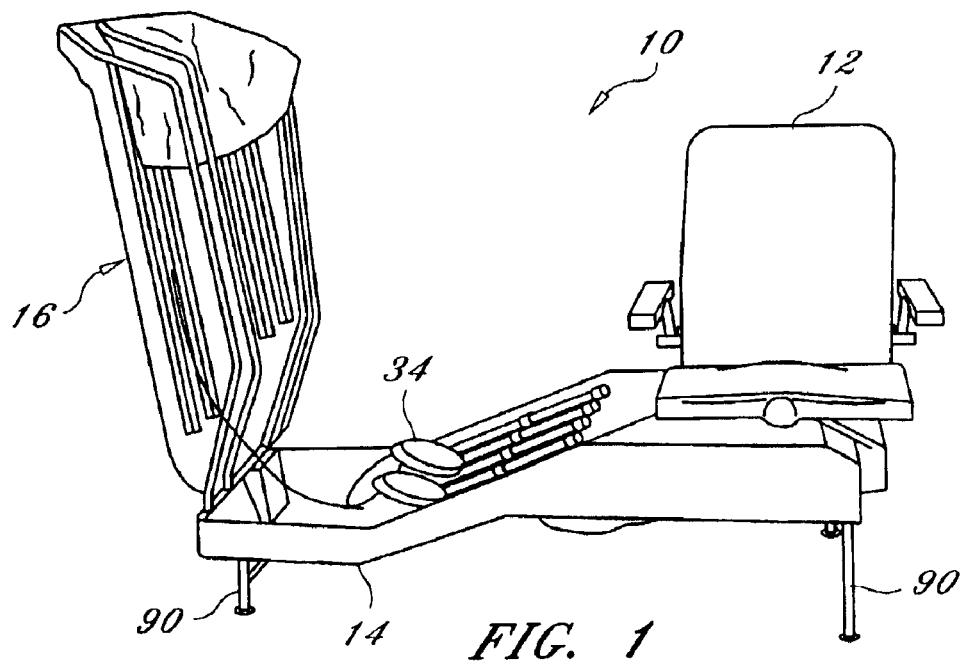
FIG. 1 shows a side view of the apparatus with the cover retracted and the chair swiveled to accept a patient.
Figure 2:
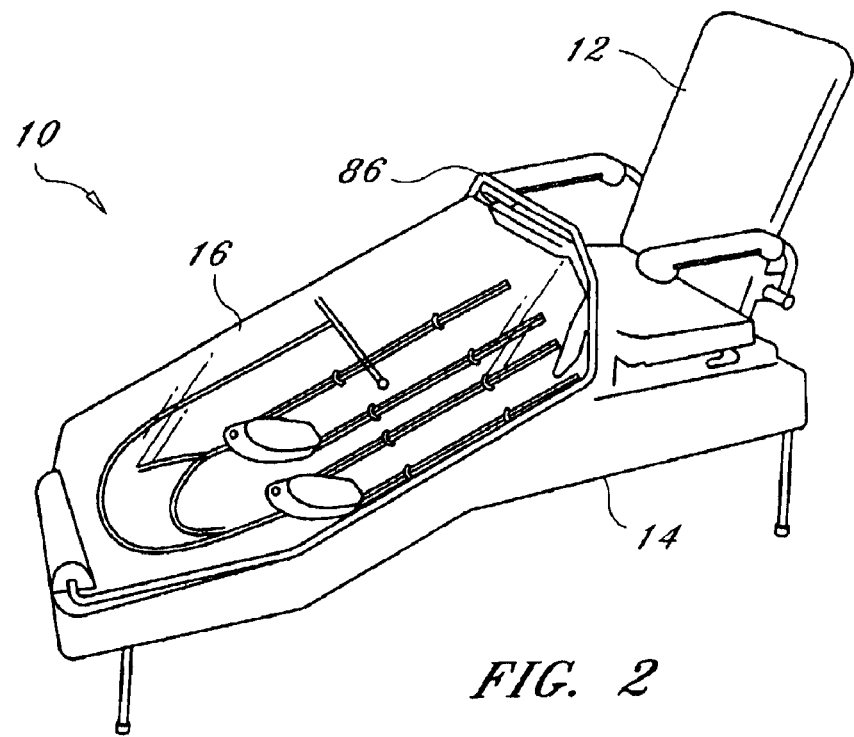
FIG. 2 shows a perspective view of the invention with the cover closed.

With reference to the drawings, FIGS. 1–11 depict the preferred embodiments of the instant invention, which comprises a vascular treatment apparatus 10. The apparatus 10 generally comprises a chair 12, a horizontal housing section 14 located below the chair 12 and a retractable cover 16.

As illustrated in FIGS. 1–4, the chair 12 is preferred to be in swiveling connection with the housing 14, to ease the placement of a patient within the apparatus 10. However, the chair 12 may be fixed in place on the housing 14. It is also preferred, for the comfort of the patient, that the chair 12 has armrests 96 and a headrest 98. It is also preferred that the seatback is adjustable. In use, for sanitary purposes, it is preferred that the chair 12 has disposable seat covers. Furthermore, a curtain 104 is preferably attached to the cover 16 to protect the patient from getting unduly wet from the treatment. The curtain is made of nylon or an equivalent material, and may also be disposable. Other means for supporting a patient, such as a contoured portion of the housing, are also contemplated and are known in the art.

Figure 4:
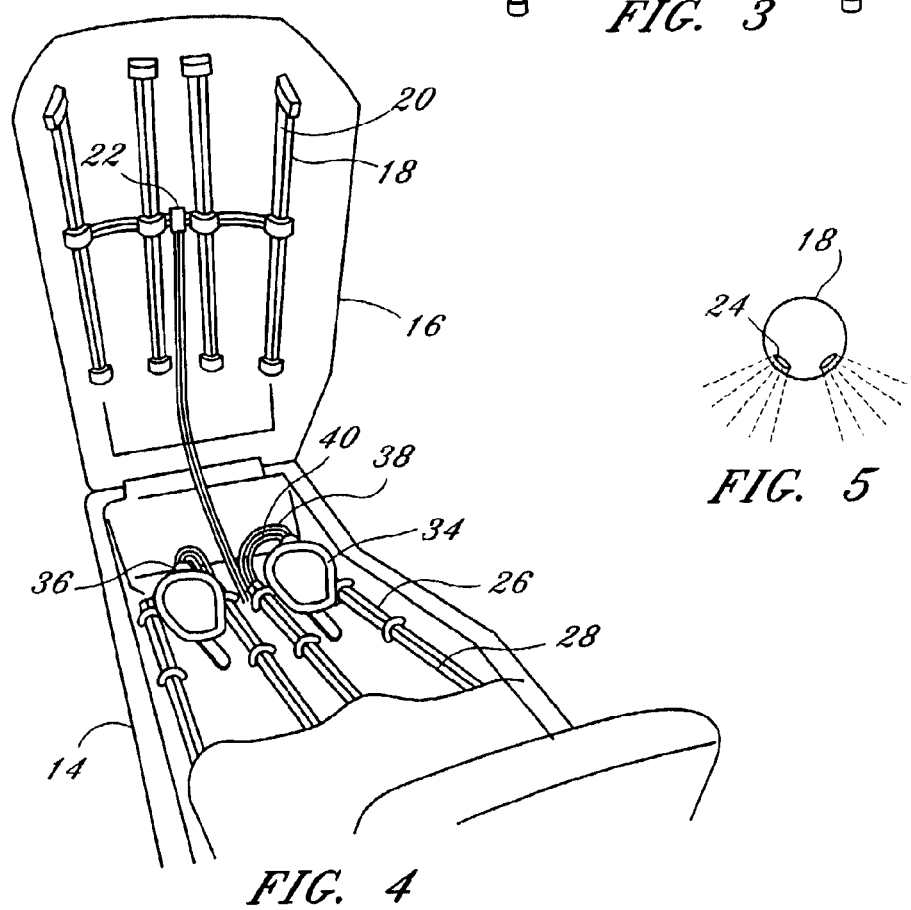
FIG. 4 shows a perspective detail view of the invention with the cover retracted.

The cover 16 may be retractable by being hinged to the housing section 14, as shown in FIGS. 1 and 4, by sliding across the housing 14 as shown in FIG. 11, or by other means known in the art. In an alternative embodiment, the cover 16 and the housing 14 are in mechanical and electronic communication so that raising the cover 16 automatically stops the operation of the apparatus 10. The retractable cover 16 is preferably transparent so that operation of the apparatus 10 can be monitored during operation; however, the cover 16 may be translucent or opaque. The cover 16 is preferably a chemical resistant plastic, although equivalent materials may be used.

Figure 5:
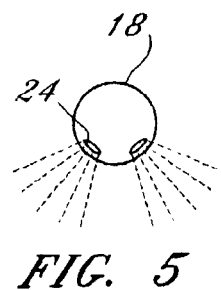
FIG. 5 shows an end view of a fluid distributor of the invention during operation.

The cover 16 includes one or more hot fluid dispensers 18 and one or more separate cold fluid dispensers 20. The dispensers 18,20 are readily shown in FIG. 4. Preferably, the dispensers 18,29 are tubular, as shown, however, other shapes, such as loops or ovals, may be desired. Furthermore, the cover 16 preferably includes one or more manifolds 22 for distributing each fluid through the dispensers 18,20. Each dispenser has nozzles 24 along its length for dispensing the fluid inside, as shown in FIG. 5. Although a hot fluid dispenser is shown in FIG. 5, the nozzles 24 are equally provided on cold fluid dispensers. Each tube has nozzles 24 on it for dispensing the carried fluid. It is through these nozzles 24 that dispensers 18,20 provide alternating and pulsating sprays of hot fluid and cold fluid to provide vascular treatment to a patient.

Figure 6:
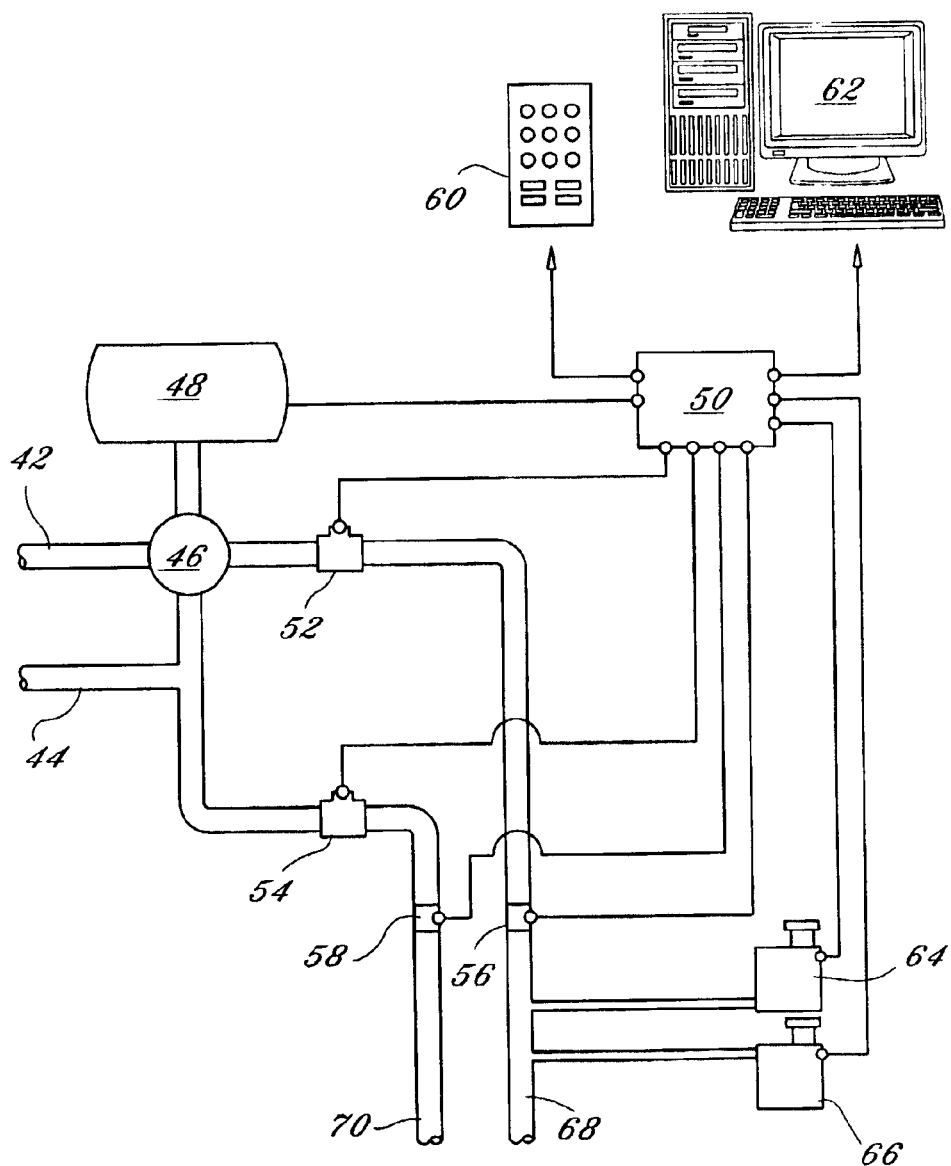
FIG. 6 shows a schematic view of the fluid distribution system and temperature and pulse controlling system of the invention.

Also in the preferred embodiment, the housing section 14 further comprises one or more housing hot fluid dispensers 26 and one or more housing cold fluid dispensers 28. These dispensers 26,28 provide improved treatment to the patient by dispensing fluid to the back of the legs of the patient being treated. As shown in FIG. 6, the housing fluid dispensers 26,28 also preferably have at least one hot fluid manifold 30 and at least one cold fluid manifold 32 for distributing fluid to the dispensers 26,28 located on the housing.

Twin tubing, or side-by-side tubing, is preferred, because it provides a more exact and distinctive temperature difference. Water is the preferred fluid for transport through the apparatus 10. However, other fluids are contemplated for use of the inventive method and apparatus, such as cold and hot mist, or cryogen processing heating and cooling. Also, for certain body areas such as the arms or torso, cold or heated gel packs may be used with the apparatus. In addition, freon type heating and cooling may be used with the apparatus.

It is also preferred that the apparatus 10 includes footrests 34 located on the housing 14. If desired, the footrests may be contoured and adjustable to conform to the length of the patient's legs. In the preferred embodiment, the footrests also include footrest nozzles 36 for added treatment to the tops of the feet of the patient. Fluid is brought to the footrest nozzles 36 via footrest feeds 38, 40.

Figure 7:
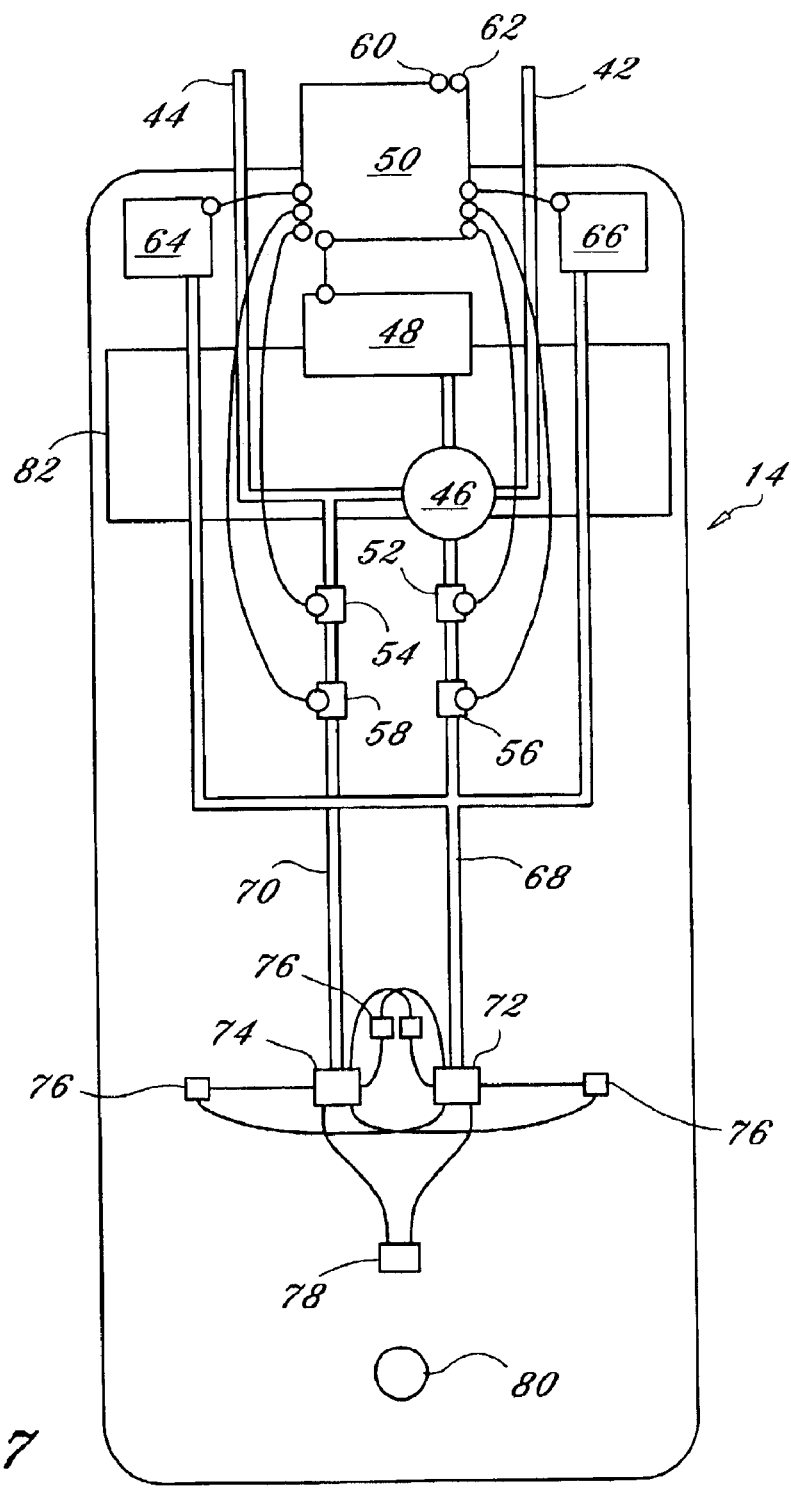
FIG. 7 shows a schematic view of the bottom of the housing of the invention

The strength and frequency of the pulsing of the sprays is preferably adjustable. The apparatus 10 preferably comprising an adjustor for the strength and frequency of the pulsing sprays. The preferred adjustment mechanism is illustrated in the schematics of FIGS. 6 and 7. A hot fluid intake 42 and a cold fluid intake 44 are provided into the apparatus 10. Hot fluid is brought to a mixing chamber 46 which is mixed by a motor 48 to adjust the temperature. The motor 48 is preferred to be on the housing, but may be on or off of the body of the housing 14. By having the motor separate from the mixing chamber, noise and vibration are reduced, thereby making the treatment more relaxing for a patient. Also, the motor and apparatus 10 are subject to less wear, thereby making the apparatus more reliable.

Temperature and pulse rate and pulse strength of the fluids are preferably controlled by a central processing unit (CPU) 50. The CPU 50 is in electronic communication with the motor 48, a hot fluid valve 52 and a cold fluid valve 54. It is preferred that the valves 52,54 are magnetic. However, equivalent valves known in the art may be used. The CPU 50 is also in electronic communication with a hot fluid thermistor 56, and may also be in communication with a cold fluid thermistor 58. In an alternative embodiment, the CPU 50 is in electronic communication with a remote control 60 or a connection to an area network 62, or both. In addition, the CPU may be connected to a main database so that data for a patient may be compared with that of other patients on the same or other treatment programs. Other equivalent adjustor means for controlling the temperature and/or the pulse rate, such as manual controls, are contemplated and known in the prior art.

Figure 10:
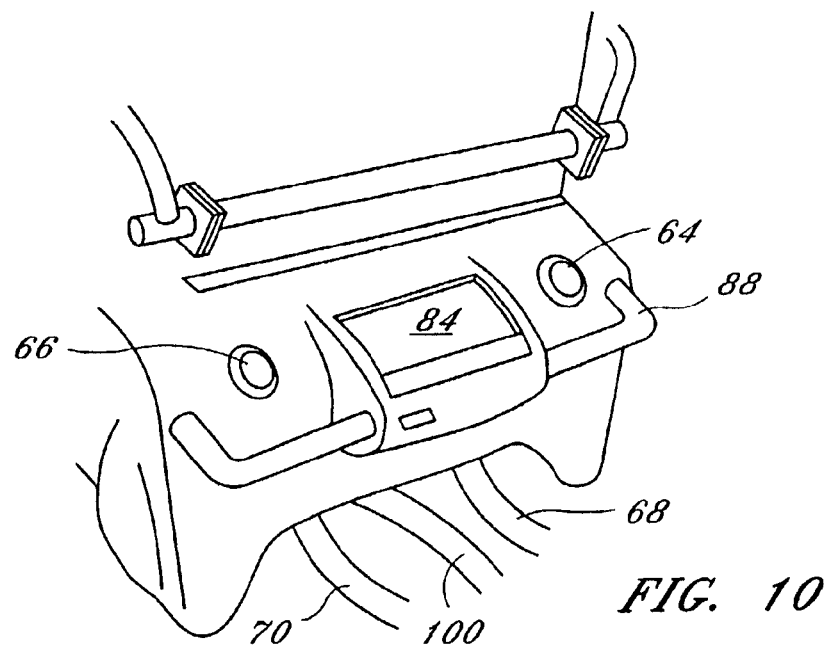
FIG. 10 shows a detail perspective view of the rear of an alternative embodiment of the invention.

As the apparatus 10 is used, the temperature of the hot fluid is sensed by the hot fluid thermistor 56. A valve (not shown) inside the mixing chamber 46 allows introduction of cold fluid in to the hot fluid stream as needed to achieve the desired temperature. The hot fluid valve 56 and the cold fluid valve 58 control pulsations of the hot fluid and the cold fluid. The cold fluid thermistor is used to keep a record of the cold fluid temperature in the memory of the CPU 50 or associated memory storage. In an alternative embodiment, one or more additives such as skin conditioner or topical cream may be added to a fluid via an additive dispenser 64 also controlled by the CPU 60. In addition, a disinfectant and/or cleaning fluid may be added to a fluid via a disinfectant dispenser 66. Although FIGS. 6 and 7 show the additive dispenser 64 and the disinfectant dispenser 66 in fluid connection with the hot fluid stream, one or both of the dispensers 64,66 may be in connection with the cold fluid stream. Intake of materials for the additive dispenser 64 and the disinfectant dispenser 66 are shown in FIG. 10.

The hot fluid and the cold fluid then are conducted to the patient via a hot fluid outlet 68 and a cold fluid outlet 70, respectively. The extension of the hot fluid outlet 68 and the cold fluid outlet 70 away from the housing 14 is shown in FIG. 10.

The CPU 50 may have a predetermined program of duration, temperature and strength of pulsation of one or both fluid streams. The program may be optimized for treatment of a particular condition or for the comfortable treatment of a particular patient. The program may be pre-programmed into the apparatus 10, or transmitted by remote control or network connection. Also, control of the treatment as it is being performed may be manually input into the apparatus 10, or transmitted by remote control or network connection.

Figure 3:
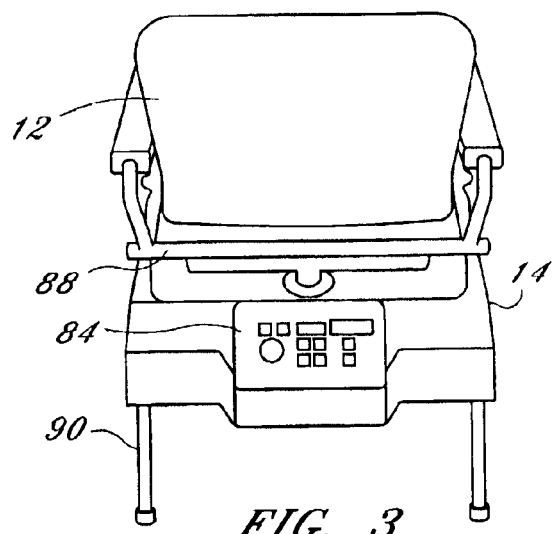
FIG. 3 shows a rear elevation view of the invention.

Furthermore, as shown, the use of skin conditioner or other additive and disinfectant may be programmed into the apparatus 10, or transmitted by remote control or network connection. Any operation that may be controlled from the apparatus is preferred to be accessible from a display 84 located behind the patient as shown in FIG. 3.

As shown in FIG. 7, in an alternative embodiment, the housing 14 includes a hot fluid manifold 72 and a cold fluid manifold 74. These manifolds 72,74 are in fluid connection with housing outlets 76 that connect to the housing fluid distributors which spray the fluid on the patient. Also, shown in this diagram for completeness, these manifolds 72,74 are in fluid connection with the manifold 78 that is attached to the cover 16 and in fluid connection with the fluid distributors attached to the cover 16. The schematic also reveals the preferred location of the drain 80 in the housing, and the mounting plate 82 for the chair 12. An outlet 100 under the housing from the drain is shown in FIG. 10.

Other equivalent means for adjusting the temperature and the pulse of the fluids are contemplated and known in the art, For example, an alternative means for adjusting the fluid temperature and pulse rate is the inclusion and incorporation of the fluid distribution system described in U.S. Pat. No. 3,487,996 to G. T. Lofgren.

In an alternative embodiment, the apparatus 10 includes a patient handlebar 86. The apparatus 10 may also include an operator handlebar 88. As shown in FIG. 10, the operator handlebar 88 may be intrinsic with a guard for the attached CPU 50 and display 84. The handlebar 88 is located behind the patient to optimize leverage, in case the position of the apparatus 10 needs to be adjusted. Also, in one embodiment the housing stands upon a plurality of legs 90. However, as shown in FIGS. 9 and 11, in an alternative embodiment one or more wheels 92 may support a portion of the housing 14. In this embodiment it may be preferred to have a brake on the wheels 92 set by a foot pedal 94, as shown in FIG. 12. Other braking means known in the art may also be used, such as a brake set by hand.

In another alternative embodiment, shown in FIGS. 9 and 11, the cover 16 slides across the horizontal housing section 14. Thus, as shown in FIG. 11, the cover 16 moves from position A to position B.

Figure 8:
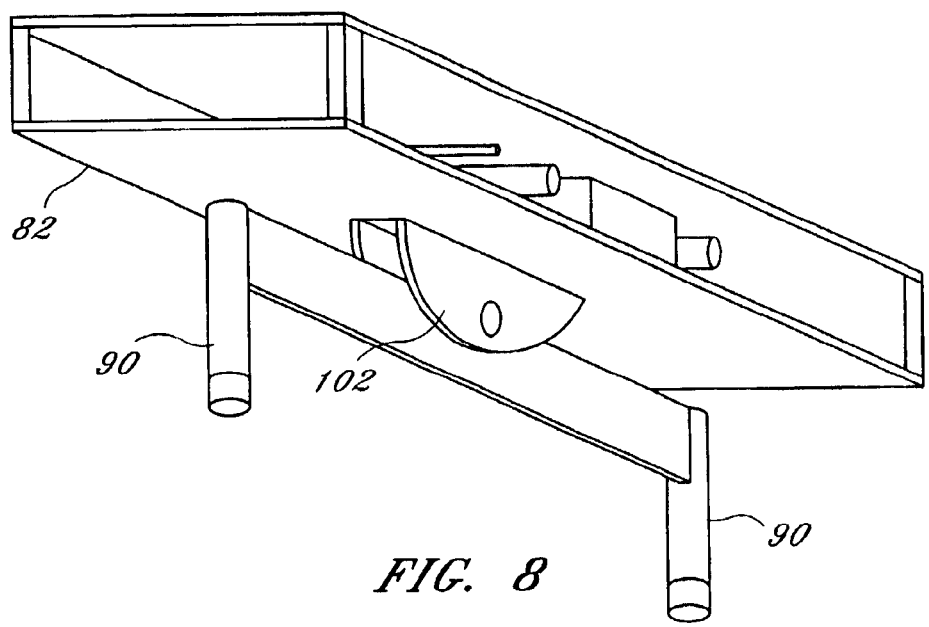
FIG. 8 shows a detail view of the mounting plate of one embodiment of the invention.

In yet another embodiment, the apparatus 10 includes means for keeping the housing level on an uneven surface. As shown in FIG. 8, the chair mounting plate 82 is connected to the legs 90, by a leveling mechanism 102. The leveling mechanism allows the housing 14 to remain level even when the legs are uneven. In still another embodiment, the legs 90 themselves are adjustable.

In the preferred embodiment for vascular treatment, the apparatus 10 is connected to cold and hot fluid lines with a minimum pressure of 35 PSI (2.46 kg/cm2), a low voltage (such as 24 Volt) alternating current power supply, and an adequate drain for the volume of fluid to be used. The patient is comfortably seated on the chair 12, and the chair 12 is swiveled so that the patient's body is in the housing 14 of the apparatus 10. The cover 16 is then closed. An ignition key is preferably used to start the apparatus 10. The key is then inserted and the treatment will then commence.

Next, it is preferred that a ready signal is displayed on the display 84 of the apparatus 10. A specific treatment program may then be selected. For example, one preferred program for vascular treatment allocates 27 minutes of operating time.

The CPU 50 of the apparatus 10 preferably records and stores complete individualized records of each patient and corresponding treatment program to assist in the evaluation process of the treatment. Furthermore, the CPU 50 can provide all information regarding leasing arrangements and for remote diagnostic evaluation.

The display panel 84 is preferably capable of illustrating any changes, such as actual temperature, pulse rate for one or both fluid streams and interval changes, during the treatment program. The display panel 84 also preferably incorporates colored optics to indicate fluid temperature and current program status. Other means for providing this information to the operator are also known in the art and may be used.

The apparatus 10 then uses a predetermined amount of time (preferably 30 seconds) to formulate a comfortable hot fluid temperature of 32 degrees centigrade. Immediately after this time, the computer begins to produce 1 second impulses of cold fluid while simultaneously rising the hot fluid temperature a few degrees within the 30 second interval.

The gradual warm-up puts the patient in a comfortable state with the fluid temperature so that the patient will not notice the constant changing of temperature or the amount of heat from the hot fluid. After the warm-up, the patient is prepared for the treatment.

The CPU 50 increases the duration of warm and cold impulses (preferably 3 seconds) to the patient over a predetermined time (preferably approximately 41 seconds). Simultaneously, the CPU 50 raises the temperature of the hot fluid and controlling the temperature in general, preferably so that the fluid does not exceed 41 degree centigrade. The treatment of hot and cold impulses then continues for approximately 25 minutes. Optionally, in the last 3 minutes of the treatment, a skin conditioner dispenser 64 may be activated if desired by the operator or patient. The inventive vascular treatment, as described, also has a depilatory effect on a patient, and may be used simply for that purpose. However, the treatment parameters may be optimized for the depilatory effect.

The full 26 minutes of this protocol (the 3 second warm and 3 second cold intervals) makes the use of the apparatus 10 to be an effective and unique treatment approach to various vascular disorders. Utilizing this unique program, the treatment (optimized hot and cold fluid intervals) has the same effectiveness on the lower extremities as any part of the human body.

For optimal results, treatments should be repeated daily for six weeks for expedient vascular treatment. Follow-up treatments are preferred to be a minimum of 4 times a year.

It is also preferred that the apparatus 10 have a self cleaning button, so that the apparatus 10 can clean and disinfect itself after the patient is taken from the apparatus 10. As stated above, it is preferred that the disinfectant dispenser 66 is located on the housing.

The operator will only need to change the seat cover and/or the curtain on the apparatus 10 for the next patient. The apparatus 10 is then ready for the next patient.

Optionally, the apparatus 10 can have a security system, requiring an ID number or a fingerprint scan, or other equivalent security measures known in the art. For repeat treatments, all or some of the security provisions may be forgone. In another embodiment, the apparatus 10, verbally greets the patient or operator, provides safety instructions, the time of day and/or counts down the commencement of the treatment.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A vascular treatment apparatus, comprising:
   means for supporting a vascular treatment patient;
   means for housing plumbing located below the means for supporting; and
   a means for covering the patient including a first means for treating a patient while on the means for supporting with alternating pulsing streams of hot fluid and cold fluid located above the means for housing.

2. The apparatus of claim 1, wherein the means for housing further comprises a second means for treating a patient on the means for supporting with alternating pulsing streams of hot fluid and cold fluid.

3. The apparatus of claim 1, wherein the second means of treating a patient includes:
   a hot fluid manifold; and
   a cold fluid manifold.

4. The apparatus of claim 1, wherein the means for housing further comprises contoured footrests.

5. The apparatus of claim 1, wherein the means for supporting is in swiveling connection with the means for housing.

6. The apparatus of claim 1, wherein the means for treating a patient includes a means for adjusting the strength and frequency of the pulsing streams.

7. The apparatus of claim 6, wherein the means for treating a patient further includes a means for controlling the temperature of at least one fluid.

8. The apparatus of claim 7, wherein the means for treating a patient further includes a means for manipulating the means for adjusting the strength and frequency of the pulsing streams and the means for controlling the temperature of at least one fluid.

9. The apparatus of claim 8, further comprising a means for sanitizing the apparatus in electronic communication with the means for manipulating the means for adjusting the strength and frequency of the pulsing streams and the means for controlling the temperature.

10. The apparatus of claim 4, wherein the footrests each further comprise means for spraying a patient's foot.

11. The apparatus of claim 1, wherein the means for covering further includes means for conveying hot and cold fluid.

12. The apparatus of claim 1, further comprising an external motor for adjusting the temperature of the hot fluid.

13. The apparatus of claim 1, further comprising a means for balancing the means for housing.

14. The apparatus of claim 1, further comprising:
   one or more front wheels on the means for housing, and
   means for locking the front wheels.

15. A vascular treatment apparatus, comprising:
   a chair;
   a horizontal housing section located below the chair; and
   a retractable cover, including:
      one or more cover hot fluid dispensers, and
      one or more cover cold fluid dispensers;
   whereby alternating and pulsating sprays of hot fluid and cold fluid treat a patient.

16. The apparatus of claim 15, wherein the housing section further comprises:
   one or more housing hot fluid dispensers; and
   one or more housing cold fluid dispensers.

17. The apparatus of claim 15, wherein the housing section further includes:
   a hot fluid manifold; and
   a cold fluid manifold.

18. The apparatus of claim 15, wherein the housing section further comprises contoured footrests.

19. The apparatus of claim 15, wherein the chair is in swiveling connection with the housing section.

20. The apparatus of claim 15, further comprising at least one adjustor for the strength and frequency of the pulsing sprays.

21. The apparatus of claim 20, further comprising a temperature controller for at least one fluid.

22. The apparatus of claim 21, further comprising a CPU for manipulating the adjustor and the temperature controller.

23. The apparatus of claim 15, further comprising a disinfectant dispenser located on the horizontal housing section.

24. The apparatus of claim 18, wherein the footrests each further comprise means for spraying a patient's foot.

25. The apparatus of claim 15, wherein the cover hot fluid dispensers and the cover cold fluid dispensers comprise separate tubes.

26. The apparatus of claim 15, further comprising an external motor for mixing hot fluid.

27. The apparatus of. claim 15, further including:
   intake for hot fluid;
   intake for cold fluid; and
   a mixing chamber located downstream from the intake for hot fluid capable of receiving cold fluid from the intake of cold fluid.

28. The apparatus of claim 15, further comprising a handlebar for the patient.

29. The apparatus of claim 15, wherein the retractable cover slides across the horizontal housing section.

30. The apparatus of claim 15, wherein the retractable cover is hingeably attached to the horizontal housing section.

31. The apparatus of claim 15, wherein the one or more hot fluid dispensers and the one or more cold fluid dispensers each further comprise at least one valve for controlling flow.

32. The apparatus of claim 23, further comprising a dispenser of skin conditioner.

33. A method for providing vascular treatment, comprising the steps of:
   placing a patient in a vascular treatment apparatus, including:
      means for supporting a vascular treatment patient;
      means for housing fluid distributors located below the means for supporting; and
      a means for covering a patient including a first means for treating a patient on the means for supporting with alternating pulsing streams of hot fluid and cold fluid located above the means for housing; and
   treating the patient with alternating pulsing streams of hot fluid and cold fluid.

34. The method of claim 33, wherein the means for housing fluid distributors further comprises a second means for treating a patient on the means for supporting with alternating pulsing streams of hot fluid and cold fluid.

35. The apparatus of claim 34, wherein the second means of treating a patient includes:
   a hot fluid manifold; and
   a cold fluid manifold.

36. The method of claim 33, wherein the step of treating comprises alternating approximately 3 seconds of hot fluid with approximately 3 seconds of cold fluid.

37. The method of claim 33, wherein the hot fluid is approximately between 32 degrees centigrade and 41 degrees centigrade.

38. The method of claim 33, wherein the duration of the step for treating is approximately 25 minutes.

39. The method of claim 33, wherein the temperature of the hot fluid is gradually raised over a pre-determined period of time before the step of treating.

40. The method of claim 33, wherein the step of treating the patient with alternating pulsing streams of hot fluid and cold fluid is controlled by a computer.

41. The method of claim 38, wherein a computer is in electronic communication with valves for controlling the flow of hot fluid and the flow of cold fluid.

42. The method of claim 33, wherein the step of treating the patient is optimized to have a depilatory effect on the patient.

* * * * *